United States Patent [19]

Al-Saadon

[11] Patent Number: 5,755,776
[45] Date of Patent: May 26, 1998

[54] PERMANENT EXPANDABLE INTRALUMINAL TUBULAR STENT

[76] Inventor: Khalid Al-Saadon, Saudi Aramco, P.O. Box 8661, Dhahran 31311, Saudi Arabia

[21] Appl. No.: 725,464

[22] Filed: Oct. 4, 1996

[51] Int. Cl.⁶ ..................... A61F 2/06
[52] U.S. Cl. ..................... 623/1; 623/12
[58] Field of Search ............ 623/1, 11, 12; 606/194, 195, 198

[56] References Cited

U.S. PATENT DOCUMENTS

| | | |
|---|---|---|
| 5,019,085 | 5/1991 | Hillstead . |
| 5,061,275 | 10/1991 | Wallsten et al. . |
| 5,102,417 | 4/1992 | Palmaz . |
| 5,133,732 | 7/1992 | Wiktor . |
| 5,195,984 | 3/1993 | Schatz . |
| 5,314,444 | 5/1994 | Gianturco . |
| 5,382,261 | 1/1995 | Palmaz . |
| 5,449,373 | 9/1995 | Pinchasik et al. . |
| 5,514,154 | 5/1996 | Lau et al. . |
| 5,545,210 | 8/1996 | Hess et al. . |
| 5,549,662 | 8/1996 | Fordenbacher ............ 623/1 |
| 5,593,442 | 1/1997 | Klein ......................... 623/1 |

Primary Examiner—John G. Weiss
Assistant Examiner—Tram Anh T. Nguyen
Attorney, Agent, or Firm—Jones, Tullar & Cooper, P.C.

[57] ABSTRACT

A permanent expandable intraluminal tubular stent supporting device intended to maintain the walls of anatomical body channels or vessels, the steno being expandable within the vessel by an angioplasty balloon associated with a catheter thereby dilating and expanding the lumen of a vessel. The stent comprises an arrangement of connecting members interconnected by a plurality of radially expandable, elongatable members. Upon inflation of the balloon, the stent expands in both radial and longitudinal directions in relation to the amount of radially-outwardly directed force by the balloon.

16 Claims, 7 Drawing Sheets

PERMANENT EXPANDABLE INTRALUMINAL TUBULAR STENT

FIELD OF THE INVENTION

The present invention relates to expandable intraluminal tubular stents which are applied within the peripheral or coronary arteries of a living animal or human being to maintain patency after a balloon angioplasty, but also relates more generally to stents which may be applied to the pathology of other anatomical canals, such as the venous, biliary and urinary canals.

DESCRIPTION OF THE PRIOR ART

Stents are generally tubular-shaped devices which function to hold open a segment of a vessel in the human body. The term "vessel" is intended to include any of the arteries and body passageways found in the human body.

Stents are of two types: the first comprising a non-elastic, metallic material which is radially expandable from the inside towards the outside under the effect of an inflatable balloon; or the second comprising an elastic metallic material made of metal meshes that are introduced stretched, i.e. under tension, into the lumen of the vessel wherein the diameter increases when the longitudinal extension, i.e. tension, is relaxed.

Further details of prior art stent structures may be found in U.S. Pat. No. 5,514,154 (Lau et al); U.S. Pat. No. 5,041,126 (Gainturo); U.S. Pat. No. 4,655,771 (Wallsten); U.S. Pat. No. 5,496,365 (Srgo); U.S. Pat. No. 5,133,732 (Wiktor); U.S. Pat. No. 5,382,261 (Palmaz); U.S. Pat. No. 5,102,417 (Palmaz); and U.S. Pat. No. 5,195,984 (Schatz). These patents are incorporated herein by reference in their entirety.

One of the difficulties encountered using known stents involves maintaining the radial rigidity needed to hold open a body lumen while at the same time maintaining the axial length of the stent. Accordingly, prior to the development of this inevention, there has been no intravascular stent capable of increasing axial length of the stent as it radially expands.

SUMMARY OF THE INVENTION

The present invention is directed to an expandable permanent tubular stent which increases in axial length as it radially expands and is relatively flexible along its longitudinal axis to facilitate its delivery to the body lumen.

The permanent expandabe intraluminal tubular stent includes an arrangement of connecting members interconnected by a plurality of radially expandable, elongatable members all disposed generally coaxially about the stents longitudinal axis. The tubular stent has a substantial uniform thin-walled thickness disposed between proximal and distal ends, a plurality of slots or axial spaces formed between opposite longitudinal ends of the connecting members. The tubular stent has an initial constricted diameter which permits intraluminal delivery into a body passageway. The stent may then be deformed by the inflation of a balloon forming part of a catheter delivery system. The balloon expands the diameter by applying a radially, outwardly directed force, wherein the expanded diameter is variable and dependent upon the amount of force applied to the tubular stent.

A further feature of the present invention is the elongation of the initial axial length of the tubular stent as it radially expands. The elongated length of the stent is variable and also dependent upon the amount of outward radial force applied to the tubular stent. The stents are preferably fabricated from low memory more plastic than elastic, biocompatible materials, for example: stainless steel 316L, gold, tantalum and similar materials, which enable the stents to be plastically deformed from their constricted diameter to their expanded diameter.

DETAILED DESCRIPTION OF THE INVENTION

Figure 1:
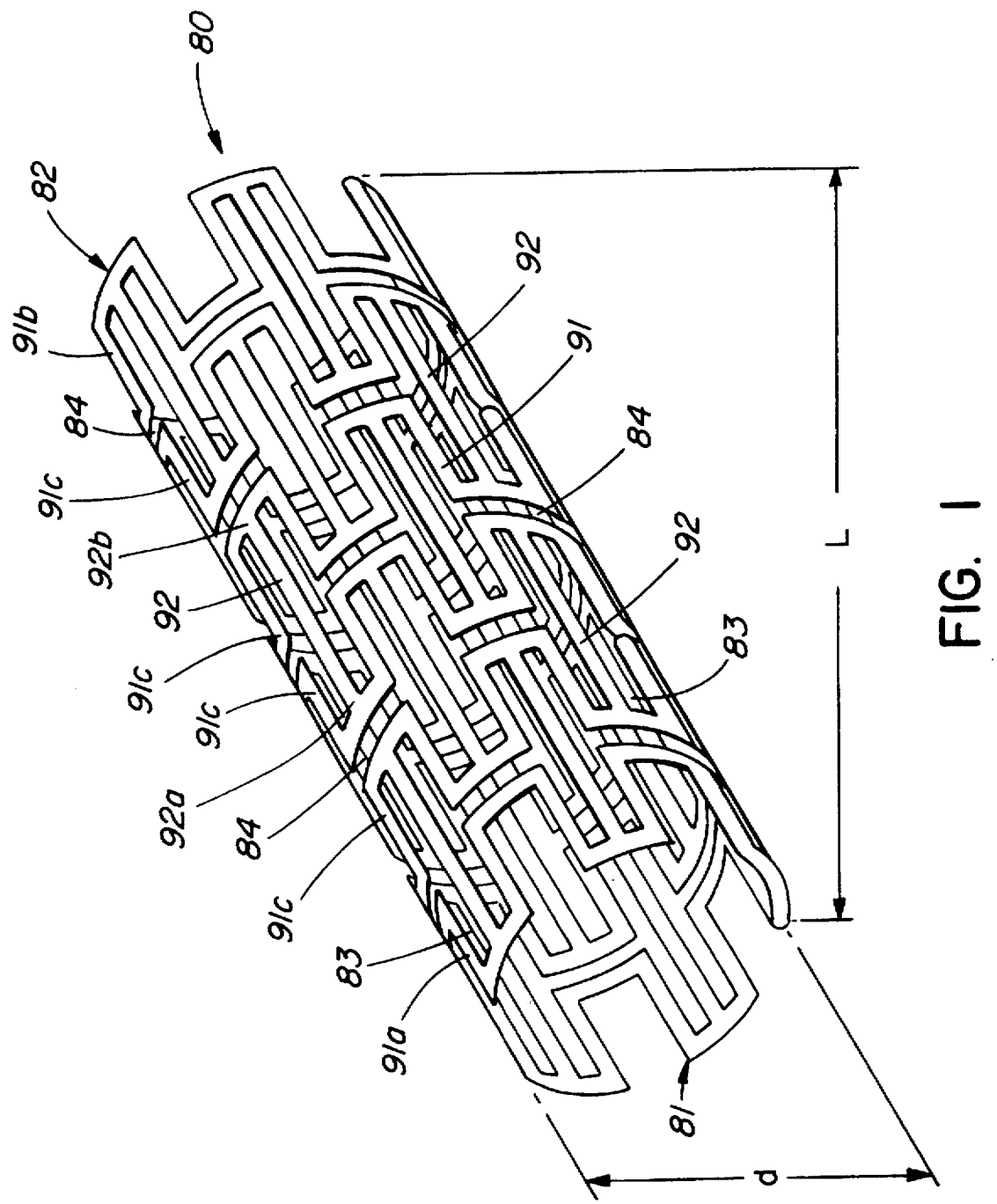
FIG. 1 is a perspective view of a permanent expandable intraluminal tubular stent, constructed and operable according to the teachings of the present invention, in its relaxed and flexible state before plastic deformation.
Figure 2:
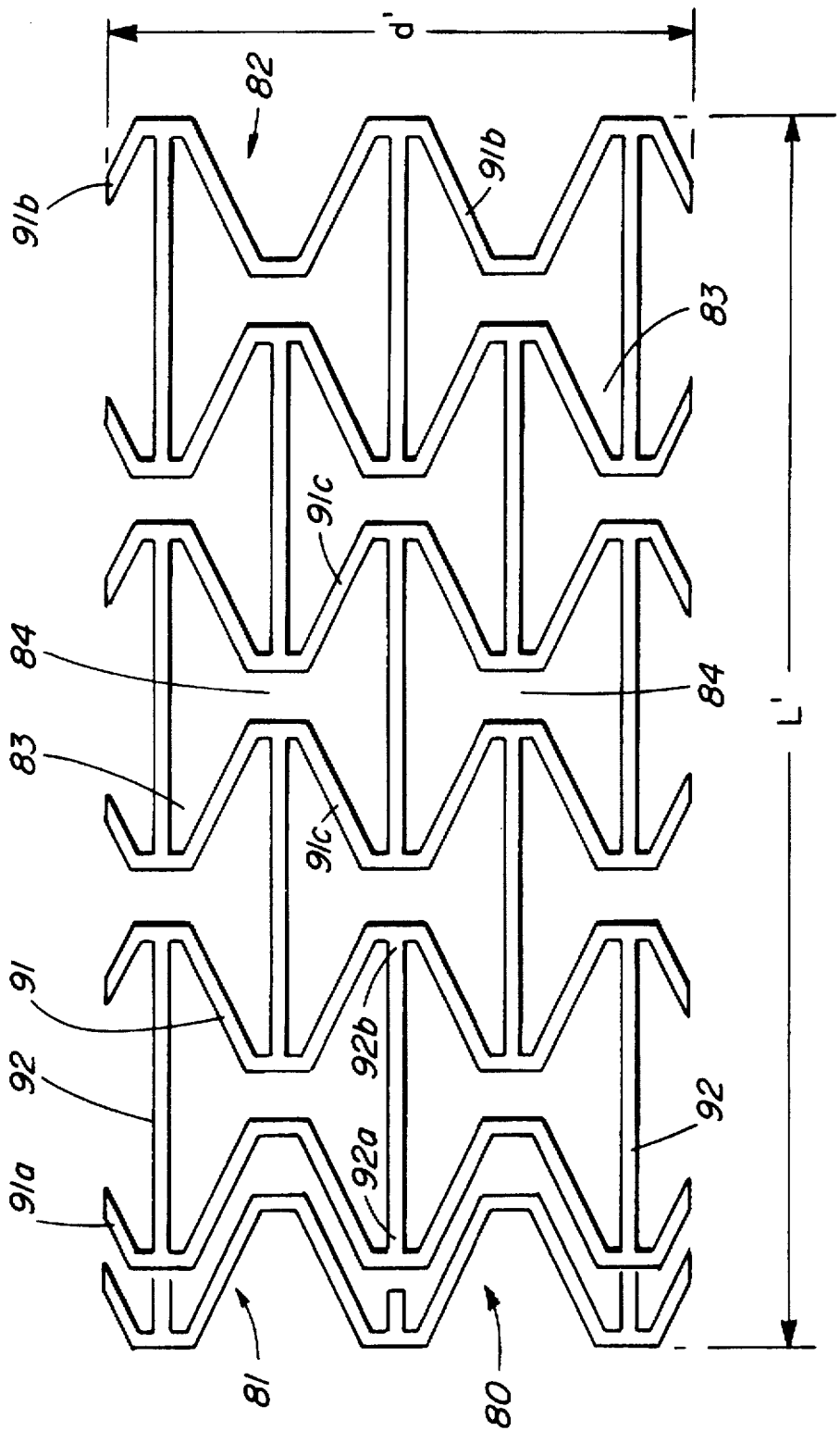
FIG. 2 is a side elevational view of the tubular stent of FIG. 1 in its expanded configuration after plastic deformation.

FIGS. 1 and 2 illustrate a permanent expandable intraluminal tubular stent 80 which generally comprises a generally cylindrical arrangement of a plurality of connecting members 92 disposed longitudinally and coaxially parallel to each other. The connecting members are oriented such that their longitudinal ends 92a are proximal a first or proximal end 81 of the stent 80 and their opposite longitudinal ends 92a are proximal the distal or second end 81 of the stent 80. The connecting members 92 are disposed in equal-numbered sets of circumferentially-spaced connecting members, with each set being axially displaced with respect to the adjacent set and with the connecting members 92 of each successive set being circumferentially-interspaced with respect to the connecting members 92 of the preceding set. In general, the ends 92a and 92b of adjacent connecting members 92 are joined together by elongatable members 91. The circumferentially-adjacent proximal ends 92a of the connecting members 92 at the proximal end 81 of the stent are attached by means of elongatable members 91a while the circumferentially-adjacent distal ends 92b of the connecting members 92 at the distal end 81 of the stent are attached by means of elongatable members 91b. The remaining distal ends 92b of each set of the connecting members 92 are attached to the proximal ends 92a of each successive set of connecting members 92 by elongating members 91c. Longitudinal ends 92a and 92b of longitudinally adjacent connecting members 92, i.e. every second set of connecting members, are axially-spaced or separated by narrow space slats 84. The tubular stent 80 has substantial uniform thin-walled thickness disposed between proximal 81 and distal 82 ends.

The tubular stent 80 has an initial constricted diameter d which permits intraluminal delivery of the tubular stent 80 into the lumen 101 of the body passageway 100 (see FIG. 3A) and is controllably "deformed" to expanded diameter d' shown in FIG. 2 application of a radially, outwardly extending force from the interior of tubular stent 80. The term "deformed" is used to indicate that the material from which tubular stent 80 is manufactured and in particular, the elongatable members 91, is subjected to a force which is greater than the elastic limit of this material. The expanded diameter d' is variable in size, which is dependent upon the amount of force applied to deform the tubular stent 80. Accordingly, the elongatable members 91a, 91c will permanently deform radially and the elongatable members 91c will permanently deform generally diagonally, moving the connecting members 92 coaxially away from each other in a radial direction. At the same time connecting members 92 will move away from each other in a longitudinal or axial direction. The connecting members 92 retain their integrity without any deformity which results in a widening of the space slots 84 between the ends 92b and 92a of longitudinally adjacent connecting members 92. This widening effect creates an elongation of the initial axial length L of the tubular stent 80 to a second axial length L' as shown in FIGS. 1 and 2.

The tubular stent 80 is preferably fabricated from biocompatible, low memory, more plastic than plastic material to permit the tubular stent 80 to be expanded and deformed from the configuration shown in FIG. 1 to the configuration shown in FIG. 2 and further to permit the tubular stent 80 to retain its expanded and deformed configuration with enlarged diameter D' and axial length L' shown in FIG. 2 and also to resist radial collapse. Suitable materials for the fabrication of the tubular stent 80 would include silver, tantalum, stainless steel, gold, titanium, NiTi alloy or any suitable plastic material, such as thermoplastic polymers, having the requisite characteristics previously described.

Figure 3A:
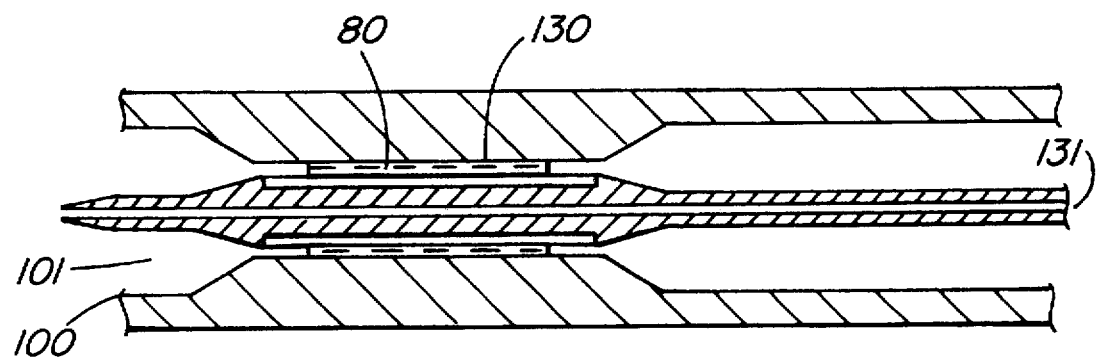
FIGS. 3A and 3B are cross-sectional views showing the scent of FIG. 1 in situ before and after expansion by a balloon forming part of its catheter delivery system.
Figure 3B:
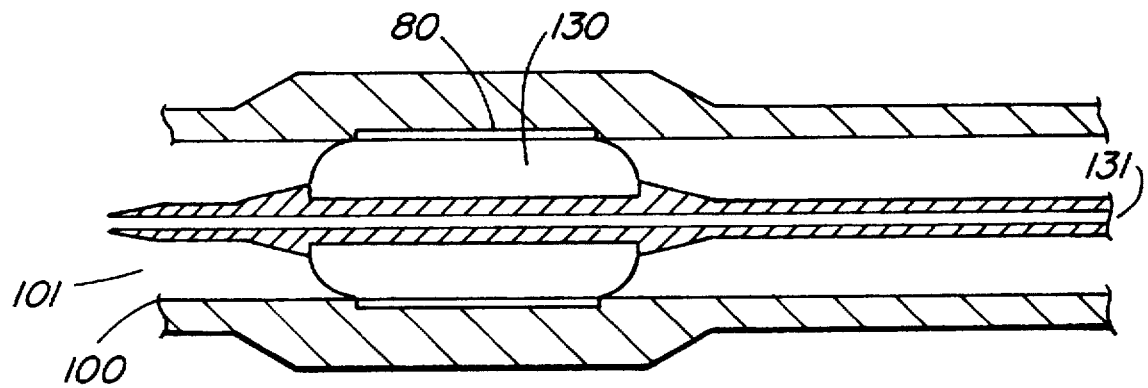

Tubular stent 80 is shown in FIGS. 3A and 3B overlying a balloon 130 forming part of its catheter delivery system 131. Tubular stint 80 is mounted on its catheter delivery system 131 in its constricted diameter state shown in FIG. 3A for plastic deformation upon inflation of a balloon 130 to its expanded diameter shown in FIG. 3B for supporting the walls 100 of a body conduit 101. The properties of the tubular stent 80 may be varied by alteration of the characteristics of elongatable members 91 and connecting members 92.

Figure 4:
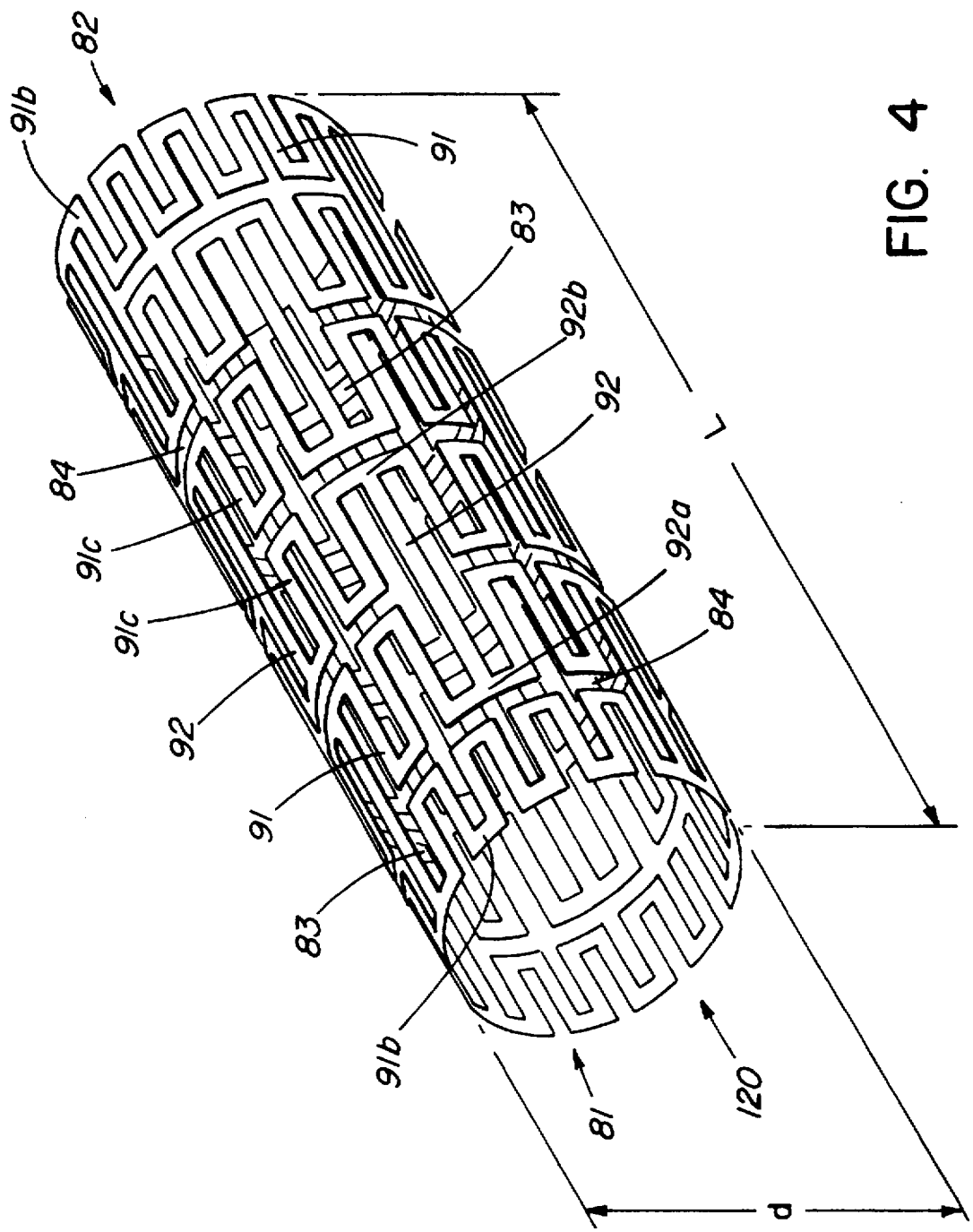
FIG. 4 is a perspective view of an alternative embodiment of the tubular stent, constructed and operable according to the teachings of the present invention, in its relaxed and flexible state before plastic deformation.
Figure 5:
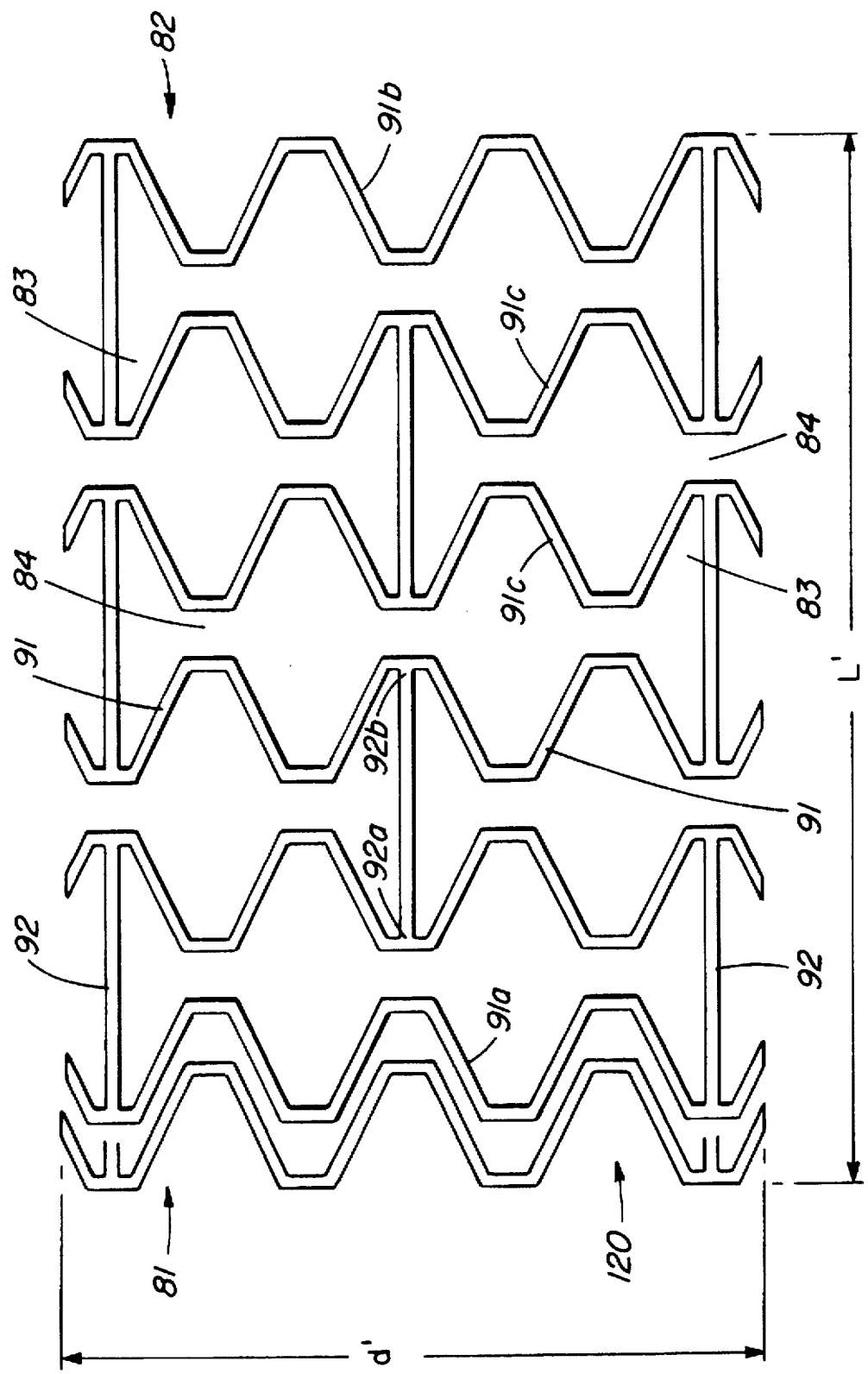
FIG. 5 is a side elevational view of the tubular stent of FIG. 4 in its expanded configuration after plastic deformation.

FIGS. 4 and 5 illustrate an alternative tubular stent 120 which generally comprises a plurality of thin-walled radially expandable elongate members 91 and connecting members 92 disposed generally the same as those of FIG. 1, wherein the elongatable members 91 of tubular stent 120 are more elongatable than those of tubular stent 80 of FIGS. 1 and 2. The elongatable members 91 of the stent 120 of FIG. 4 comprise a plurality of intermediate sections arranged in a serpentine pattern whereas the elongating members of the stent 80 of FIG. 1 comprise three intermediate sections arranged at right angles. This will achieve more flexibility for tubular stent 120.

Figure 6:
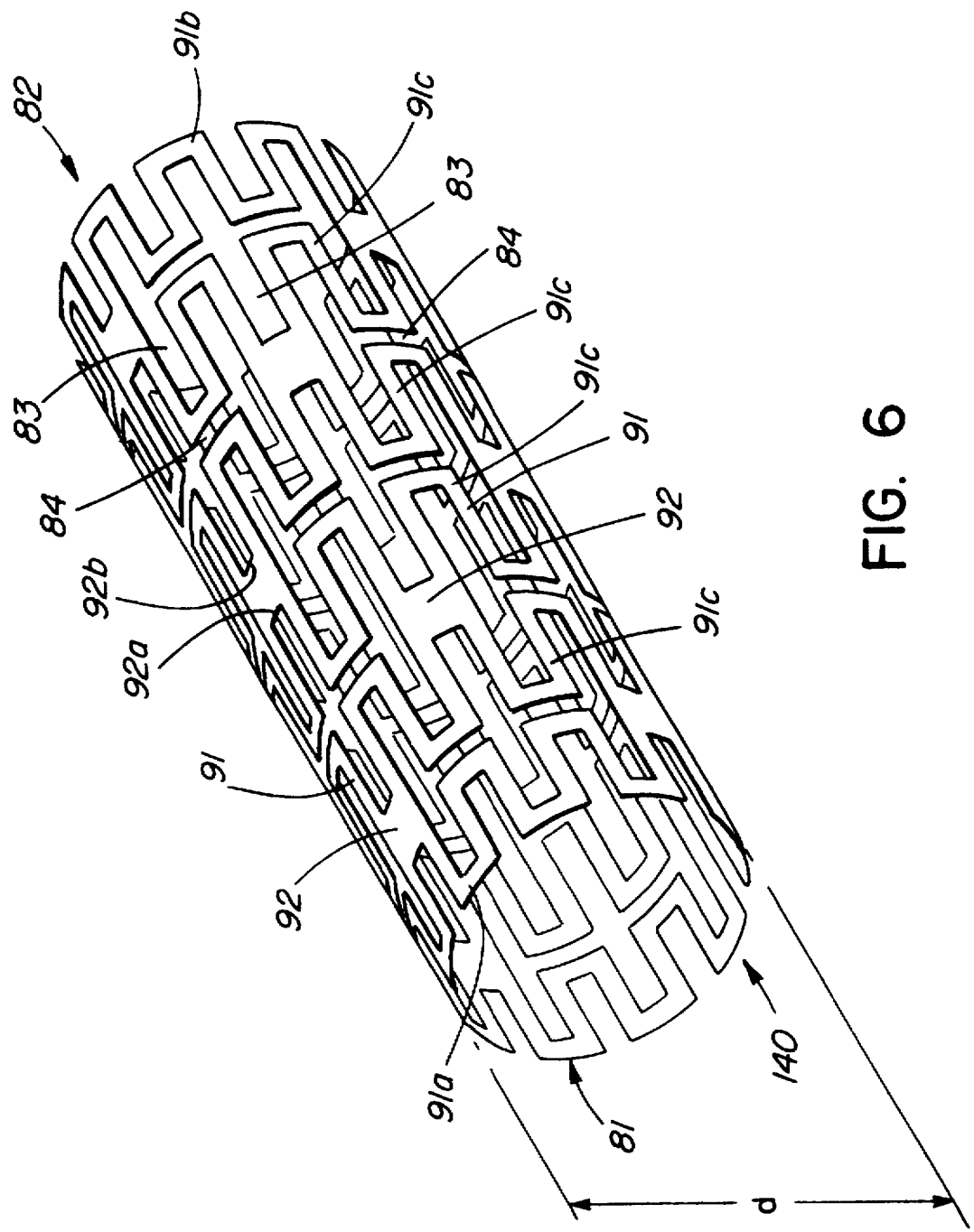
FIG. 6 is a perspective view of another alternative embodiment of the tubular stent, constructed and operable according to the teachings of the present invention, in its relaxed and flexible state before plastic deformation.
Figure 7:
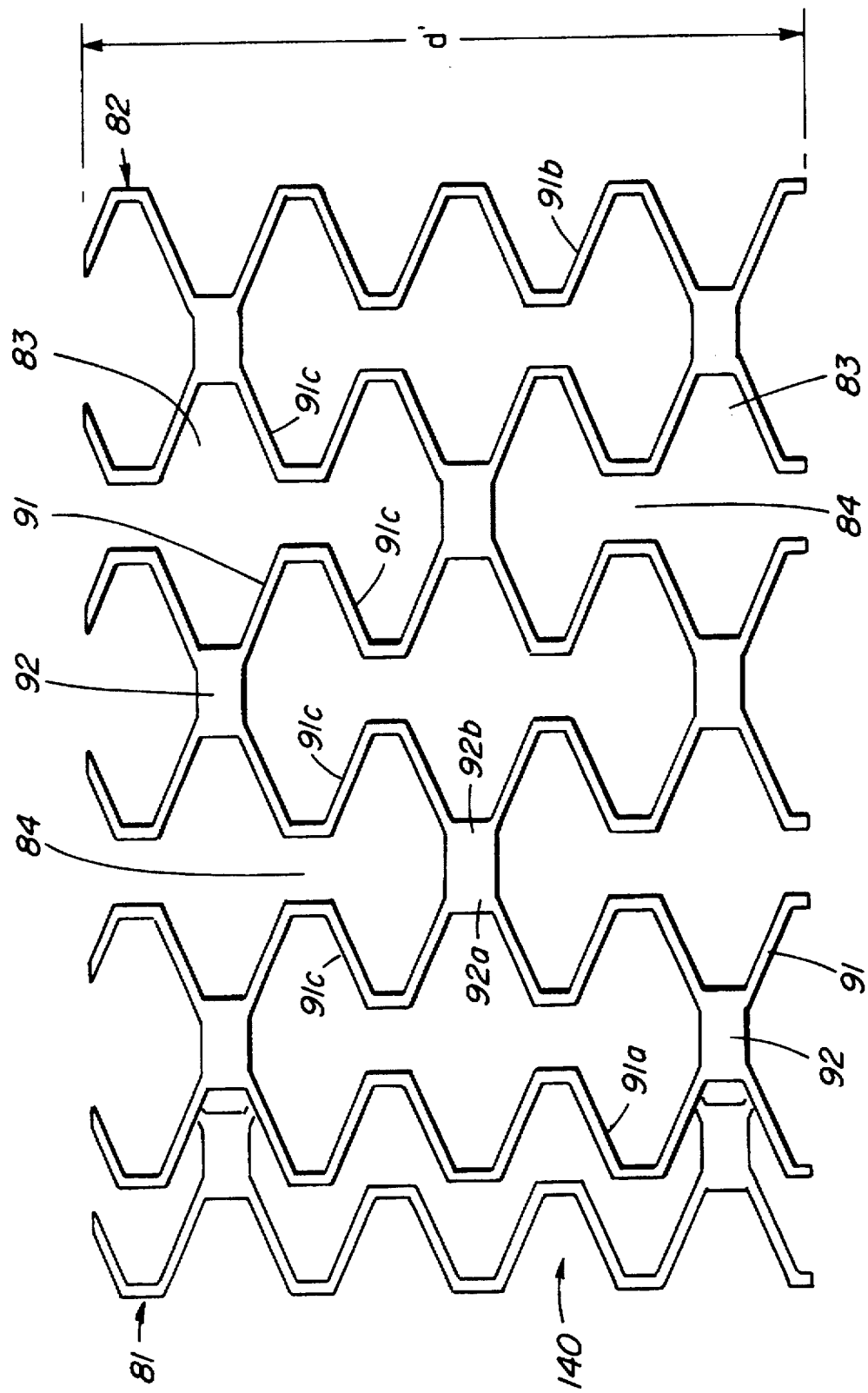
FIG. 7 is a side elevational view of the tubular stent of FIG. 6 in its expanded configuration after plastic deformation.

FIGS. 6 and 7 illustrate another alternative tubular stent 140 which is similar to the previous embodiments but wherein the connecting members 92 are relatively shorter and square shaped and wherein the connecting members of each successive set are axially-spaced. Preferably, the elongated length of the elongatable members of stent 140 is approximately ten times the longitudinal length of the connecting members of stent 140, whereas the elongated length of the elongatable members of stents 80 and 120 are approximately half the longitudinal length of the connecting members of the respective stents 80, 120. This will achieve more flexibility for tubular stent 140 which is particularly important for delivery through blood vessels having multiple curved portions.

It is to be understood that the invention has been described with respect to a limited number of embodiments. It will be appreciated that many variations, modifications and other applications of the invention may be made. Accordingly, the invention is therefore to be limited only by the scope of the appended claims.

I claim:

1. A permanent, expandable tubular stent comprising:
   a uniform arrangement of connecting members in a cylindrical configuration of an initial length and of an initial diameter about a longitudinal axis, each connecting member having a proximal end and a distal end and being oriented with said proximal end nearer a first end of said stent than said distal end which is nearer an opposite, second end of said stent, the arrangement of connecting members comprising:
   at least three sets each of an equal plurality of circumferentially-spaced connecting members, each said set being coaxially-arranged along a longitudinal axis and being axially displaced a predetermined distance from a each adjacent set, the connecting members of each successive set being radially-interspaced with respect to the connecting members of the preceding set with said predetermined distance being such that the proximal ends of the connecting members of each successive set overlap the distal ends of the connecting members of the preceding set;
   a plurality of first elongatable members each disposed between the proximal ends of each pair of circumferentially-adjacent connecting members of the first set;
   a plurality of second elongatable members each disposed between the distal ends of each pair of circumferentially-adjacent members of the last set;
   a plurality of third elongatable members each disposed between the distal ends of the connecting members of each set and the proximal end of each circumferentially-adjacent connecting member of each successive set;
   said first, second and third elongatable members being sufficiently plastically deformable such that internal application of a generally uniformly-distributed, radically outwardly directed force causes said first and second elongatable members to radially expand and said third elongatable members to deform and elongate uniformly in a radially diagonal direction, thereby causing the connecting members of each set to move radially outwardly while the connecting members of adjacent sets move axially away from one another, thus, increasing the length of the stent from said initial length and the diameter of the stent from said initial diameter in relation to the amount of said radially outwardly directed force,
   said stent being flexible about said longitudinitial axis and said initial diameter being such as to permit intraluminal delivery of said stent into a body passageway.

2. The stent of claim 1, wherein each said first, second and third elongatable member consists of a plurality of intermediate sections joined at right angles.

3. The stent of claim 1, wherein each said first, second and third elongatable member consists of a plurality of intermediate sections arranged in a serpentine pattern.

4. The stent of claim 1, wherein said connecting members and said first, second and third elongatable members are integrally formed and have uniform thin-walled thickness in the radial direction.

5. The stent of claim 4, wherein said connecting members and said first, second and third elongatable members are formed from the same material.

6. The stent of claim 5, wherein said material is a low-memory, more plastic than elastic, bio-compatible material.

7. The stent of claim 6, wherein the material is selected from the group of materials consisting of stainless steel, silver, gold, tantalum, titanium, NiTi alloy and thermoplastic polymers.

8. The stent of claim 1, wherein the elongated length of the third elongatable members is approximately half the longitudinal length of the connecting members.

9. A permanent, expandable tubular stent comprising:

a uniform arrangement of connecting members in a cylindrical configuration of an initial length and of an initial diameter about a longitudinal axis, each connecting member having a proximal end and a distal end and being oriented with said proximal end nearer a first end of said stent than said distal end which is nearer an opposite, second end of said stent, the arrangement of connecting members comprising:

at least three sets each of an equal plurality of circumferentially-spaced connecting members, each said set being coaxially-arranged along a longitudinal axis and being axially displaced a predetermined distance from each adjacent set, the connecting members of each successive set being radially-interspaced with respect to the connecting members of the preceding set with said predetermined distance being such that the proximal ends of the connecting members of each successive set are axially-spaced from the distal ends of the connecting members of the preceding set;

a plurality of first elongatable members each disposed between the proximal ends of each pair of circumferentially-adjacent connecting members of the first set;

a plurality of second elongatable members each disposed between the distal ends of each pair of circumferentially-adjacent members of the last set;

a plurality of third elongatable members each disposed between the distal ends of the connecting members of each set and the proximal end of each circumferentially-adjacent connecting member of each successive set;

said first, second and third elongatable members being sufficiently plastically deformable such that internal application of a generally uniformly-distributed, radially outwardly directed force causes said first and second elongatable members to radially expand and said third elongatable members to deform and elongate uniformly in a radially diagonal direction, thereby causing the connecting members of each set to move radially outwardly while the connecting members of adjacent sets move axially away from one another, thus, increasing the length of the stent from said initial length and the diameter of the stent from said initial diameter in relation to the amount of said radially outwardly directed force, said stent being flexible about said longitudinitial axis and said initial diameter being such as to permit intraluminal delivery of said stent into a body passageway.

10. The stent of claim 9, wherein each said first, second and third elongatable member consists of a plurality of intermediate sections joined at right angles.

11. The stent of claim 9, wherein each said first second and third elongatable member consists of a plurality of intermediate sections arranged in a serpentine pattern.

12. The stent of claim 9, wherein said connecting members and said first, second and third elongatable members are integrally formed and have uniform thin-walled thickness in the radial direction.

13. The stent of claim 12, wherein said connecting members and said first, second and third elongatable members are formed from the same material.

14. The stent of claim 13, wherein said material is a low-memory, more plastic than elastic, bio-compatible material.

15. The stent of claim 14, wherein the material is selected from the group of materials consisting of stainless steel, silver, gold, tantalum, titanium, NiTi alloy and thermoplastic polymers.

16. The stent of claim 9, wherein the elongated length of the third elongatable members is approximately ten times the longitudinal length of the connecting members.

* * * * *